United States Patent [19]

O'Brien, Jr.

[11] 4,456,753

[45] Jun. 26, 1984

[54] PROCESS FOR THE MANUFACTURE OF HIGHLY CRYSTALLINE SODIUM CEFOPERAZONE

[75] Inventor: Daniel J. O'Brien, Jr., Canterbury, Conn.

[73] Assignee: Pfizer Inc., New York, N.Y.

[21] Appl. No.: 464,223

[22] Filed: Feb. 7, 1983

[51] Int. Cl.$^3$ .......................................... C07D 501/12
[52] U.S. Cl. ........................................ 544/20; 544/27
[58] Field of Search .................................. 544/20, 27

[56] References Cited

U.S. PATENT DOCUMENTS 4,087,424  5/1978  Saikawa et al. ..................... 424/246

FOREIGN PATENT DOCUMENTS 1508071  4/1978  United Kingdom ............... 424/246

Primary Examiner—Paul M. Coughlan, Jr.
Attorney, Agent, or Firm—Charles J. Knuth; Peter C. Richardson

[57] ABSTRACT

A process for the preparation of highly crystalline sodium cefoperazone comprising the controlled addition of acetone to a water/acetone/sodium cefoperazone solution and subsequent separating and drying the resulting crystalline sodium cefoperazone.

4 Claims, No Drawings

PROCESS FOR THE MANUFACTURE OF HIGHLY CRYSTALLINE SODIUM CEFOPERAZONE

BACKGROUND OF THE INVENTION

This invention relates to a novel, convenient and economic process for producing sodium cefoperazone. More particularly, it relates to the production of highly crystalline sodium cefoperazone.

Cefoperazone is a broad spectrum beta-lactam antibiotic usually adminstered parenterally as the sodium salt, which is provided by the available procedures (British Patent Specification No. 1,508,071) as an amorphous solid.

Amorphous compounds are, in general less desirable than are crystalline forms thereof, from the standpoint of preparation, storage and use. A crystalline compound is generally considerably more stable than an amorphous form of the compound, and resists decomposition and discoloration. For pharmaceutical use, it is much easier to prepare dosage forms from crystalline compounds than from those in amorphous form. Finally, amorphous compounds are frequently more hygroscopic than those in crystalline form.

SUMMARY OF THE INVENTION

A relatively simple, inexpensive process has now been discovered to obtain highly crystalline sodium cefoperazone essentially free of residual organic solvents, comprising the steps of combining a water-/acetone/cefoperazone solution (1-1.5, 2.0-5.0, 1.0; v. v, w) with sufficient acetone to provide a water/acetone solution containing from about 14% to 17% water v/v, at about 5° to 25° C. with a preferred temperature of 18°-25° C. adding sufficient acetone to the resulting slurry to provide a water/acetone solution containing from about 3% to 5% water v/v, based on acetone level; and separating the resulting crystalline sodium cefoperazone.

The initial water/acetone/sodium cefoperazone solution may be prepared by combining appropriate amounts of an acetone solution of cefoperazone free acid with an aqueous solution containing about one equivalent of a base selected from sodium bicarbonate, sodium carbonate and sodium 2-ethyl hexanoate.

The highly crystalline product may be separated by filtration or centrifugation and dried under vacuum (0.1 to 10 mm Hg) at about 25° C.

DETAILED DESCRIPTION OF THE INVENTION

Highly crystalline sodium cefoperazone may be prepared by the controlled staged addition of acetone to an initial water/acetone/sodium cefoperazone solution of the composition 1.0-1.5, 2.0-5.0, 1.0 v, v, w. The aforementioned initial sodium cefoperazone solution is preferably formed in situ by combining appropriate amounts of an acetone solution of cefoperazone free acid with an aqueous solution of about one equivalent of a basic sodium salt compound, selected from the group consisting of sodium bicarbonate, sodium carbonate, and sodium 2-ethylhexanoate.

Acetone is added to the initial aqueous acetone solution of sodium cefoperazone until the water content is reduced to 14-17% of the acetone volume at a temperature of 5°-25° C., with a preferred temperature range of 18°-25° C., producing a ratio of water/acetone/sodium cefoperazone solution of 1.0-1.5, 7.0-12.0, 1.0 v, v, w.

The solution is then stirred until a haze develops, and stirring continued until a thick slurry has formed. Further acetone is then added, with stirring in the aforementioned temperature range until a final water content of 3-5% of the acetone level is obtained. The resulting crystals of sodium cefoperazone can be collected by conventional means, preferably by centrifugation or vacuum filtration, and, if desired washed with available organic solvent, preferably 3% water/acetone solution, then with acetone or ethanol, and dried. The product is preferably dried at about 25°-50° C., preferably under a vacuum of about 0.1 to 10 mm Hg, for about 1 to 20 hours.

The process of the present invention allows for the formation of highly crystalline sodium cefoperazone. By highly crystalline is meant a crystalline product that is substantially free of amorphous material. The process of the present invention also results in highly crystalline sodium cefoperazone which is essentially free of residual organic solvents, without requiring extraordinary drying conditions to reduce the amount of organic solvent to a range acceptable for human use.

Sodium cefoperazone is a broad spectrum antibiotic useful in treating bacterial infections is humans. The crystalline sodium cefoperazone produced by the process of this invention is used in the same manner as the amorphous product described in the art including British Patent Specification No. 1,508,071 and U.S. Pat. No. 4,087,424. The highly crystalline sodium cefoperazone produced by the present process is more stable, less subject to undesirable decomposition and more conveniently handled and incorporated in pharmaceutical dosage forms than the amorphous material.

The present invention is illustrated by the following examples. It will, however, be understood that the invention is not limited to the specific details and conditions of these examples.

EXAMPLE I 10 g. of partially crystalline sodium cefoperazone was dissolved in 15 ml. of water at a temperature of 20°-25° C. To the stirred solution 106 ml of acetone was added at a temperature of 20°-25° C., resulting in a slight haze. The hazy solution was stirred at 18°-21° C. until a thick slurry developed. After the thick slurry developed 325 ml of acetone was added over 2 hours. The final water content was measured at 3-4% of acetone content. Stirring was continued for 5 hours at 20°-25° C., and the resulting crystals of sodium cefoperazone were collected by vacuum filtration, 8.9 g. yield.

EXAMPLE II

A slurry of 25 g of cefoperazone free acid in 75 ml. acetone at 20°-25° C. was treated with a solution of 3.08 g. sodium bicarbonate in 37.5 ml. of water with stirring to adjust the pH to 6.5-6.8 at 20°-25° C. The resulting solution was clarified and 170 ml. of acetone was added over a half hour at 20°-25° C. until a slight haze resulted. The hazy solution was stirred at 20°-25° C. for about 2 hours until a thick slurry developed. 640 ml. of acetone was then added over 2 hours, maintaining the temperature of 20°-25° C. Stirring continued for 5 hours at 20°-25° C. and the crystals were collected by vacuum filtration, 21.5 g. yield.

I claim:

1. A process for preparing highly crystalline sodium cefoperazone which comprises the steps of (a) combining a water/acetone/sodium cefoperazone solution (1–1.5, 2.0–5.0, 1.0; v, v, w) with sufficient acetone to provide a water/acetone solution containing from about 14% to about 17% (v/v) water based or acetone level at a temperature of about 5°–25° C., (b) adding sufficient acetone to the resulting slurry to provide a water/acetone solution containing from about 3% to 5% water based on acetone level; (c) and separating the resulting crystalline sodium cefoperazone from said slurry.

2. The process of claim 1 wherein said temperature is 18°–25° C.

3. The process of claim 1, wherein said water/acetone/sodium cefoperazone solution is formed in situ by combining an acetone solution of cefoperazone free acid with an aqueous solution containing about one equivalent of a base selected from the group consisting of sodium bicarbonate, sodium carbonate and sodium 2-ethylhexanoate.

4. The process of claim 1, wherein said crystalline sodium cefoperazone is dried under vacuum at about 25° to 50° C.